(12) United States Patent
Rodriquez

(10) Patent No.: US 6,428,316 B1
(45) Date of Patent: Aug. 6, 2002

(54) TARTAR TRAP

(76) Inventor: Guillermo P. Rodriquez, 5790 Castlegate Ave., Davie, FL (US) 33331

( * ) Notice: Subject to any disclaimer, the term of this patent is extended or adjusted under 35 U.S.C. 154(b) by 0 days.

(21) Appl. No.: 09/766,447

(22) Filed: Jan. 18, 2001

(51) Int. Cl.$^7$ .............................................. A61C 17/06
(52) U.S. Cl. ...................................... 433/92; 604/319
(58) Field of Search ............................. 433/92, 91, 95; 604/319, 317

(56) References Cited

U.S. PATENT DOCUMENTS

| 4,083,706 | A | * | 4/1978 | Wiley ........................... 55/385 |
| 4,806,101 | A | * | 2/1989 | Rossi ........................... 433/92 |
| 5,437,651 | A |   | 8/1995 | Todd et al. .................. 604/313 |
| 5,630,939 | A | * | 5/1997 | Bulard ...................... 210/416.1 |
| 5,779,649 | A |   | 7/1998 | Herbert ....................... 600/571 |
| 6,183,254 | B1 | * | 2/2001 | Cohen ......................... 433/92 |

* cited by examiner

*Primary Examiner*—Nicholas D. Lucchesi
*Assistant Examiner*—Melba Bumgarner
(74) *Attorney, Agent, or Firm*—McHale & Slavin

(57) ABSTRACT

A dental suction wand is used to collect tartar and particulate material during the dental procedure of cleaning teeth. The wand has a large diameter body with a small diameter suction tip connected at one end and an suction hose connected at the other end. The large diameter body forms a discontinuity in the fluid flow by which the particulate material is separated and entrapped in the body. A removable filter may be used to remove the particulate material from the wand for exhibit and explanation by the dentist.

11 Claims, 1 Drawing Sheet

TARTAR TRAP

FIELD OF THE INVENTION

This invention is related to the field of dentistry. Specifically, the invention is directed to a hand held suction wand having a debris trap.

BACKGROUND OF THE INVENTION

It is estimated that over 70 per cent of adults have some form of periodontal disease. As our population ages, more and more adults will be found with periodontal problems.

If a simple way could be found to motivate people into taking better care of their teeth, we will see an improvement in the degree of periodontal disease.

This invention is directed toward an apparatus that can be used by the dentist or dental hygienist to show patients the material which is largely responsible for causing gum infections. By collecting this material, tartar, and showing the patient-the amount that is collected from beneath the gums and around the teeth, the patient may be motivated to improve their oral nygiene habits. This visual presentation may give the patient a better understanding of the importance of professional assistance on a regular basis.

DESCRIPTION OF THE PRIOR ART

Almost any dentist's office has a conventional suction system with a hand held instrument for insertion into the mouth for removal of air, saliva, blood and other solid debris. Usually, the system includes a remote suction pump of some type connected to the hand held wand. The suction pump has a waste line into which the biological materials are conveyed for sanitary disposal.

U.S. Pat. No. 2,822,808 to Boone teaches the use of a suction wand with a small diameter collection end connected to an enlarged diameter portion. The enlarged diameter portion is connected at the other end to a suction line. The enlarged diameter portion forms a collection chamber for collecting specimen from the surgical wand.

U.S. Pat. No. 5,437,651 to Todd et al teaches the use of a suction wand having an absorbent material covering the entrance of the suction tube. The absorbent material collects debris to prevent inclusion with the fluids that progress through the suction wand.

U.S. Pat. No. 5,779,649 to Herbert teaches a suction wand with a small diameter entrance and an enlarged portion connected to a suction source. Inside the enlarged portion is filter to trap particulate waste that cannot pass through the apertures of the filter.

What is lacking in the prior art is a teaching of collecting certain debris for exposure, examination and explanation for the patient to educate the patient.

SUMMARY OF THE INVENTION

A dental suction wand is used to collect tartar and particulate material during the dental procedure of cleaning teeth. The wand has a large diameter body with a small diameter suction tip connected at one end and an suction hose connected at the other end. The large diameter body forms a discontinuity in the fluid flow by which the particulate material is separated and entrapped in the body. A removable filter may be used to remove the particulate material from the wand for exhibit and explanation by the dentist.

Accordingly, it is an objective of the instant invention to teach a dental suction wand with a trap for separating and capturing particulate material entrained in the waste fluid removed from the mouth during dental procedures, such as cleaning teeth.

It is a further objective of the instant invention to teach a transparent trap for visual examination of the particulate waste material.

It is yet another objective of the instant invention to teach a removable fluid filter located within the trap. After the dental procedure, the filter is removed from the trap and displayed for examination of the tartar and debris collected from the patient's teeth.

Other objectives and advantages of this invention will become apparent from the following description taken in conjunction with the accompanying drawings wherein are set forth, by way of illustration and example, certain embodiments of this invention. The drawings constitute a part of this specification and include exemplary embodiments of the present invention and illustrate various objects and features thereof.

DESCRIPTION OF THE INVENTION

Figure 1:
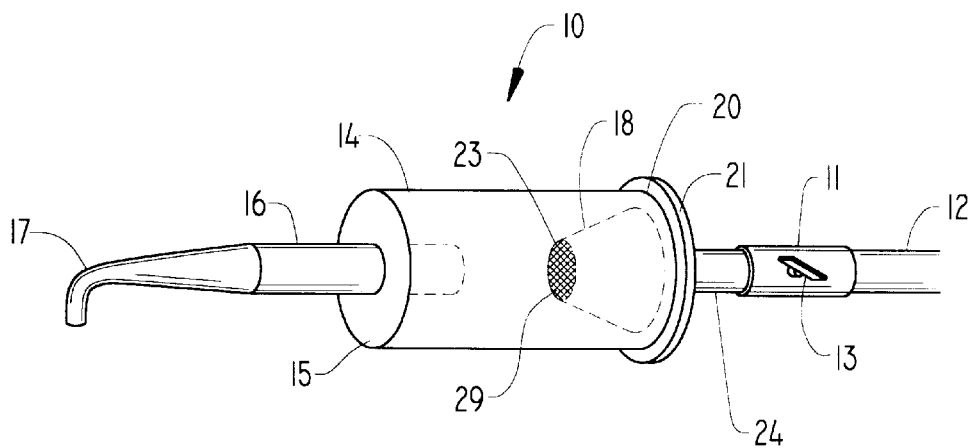
FIG. 1 is a perspective of the dental wand and trap of the invention.
Figure 2:
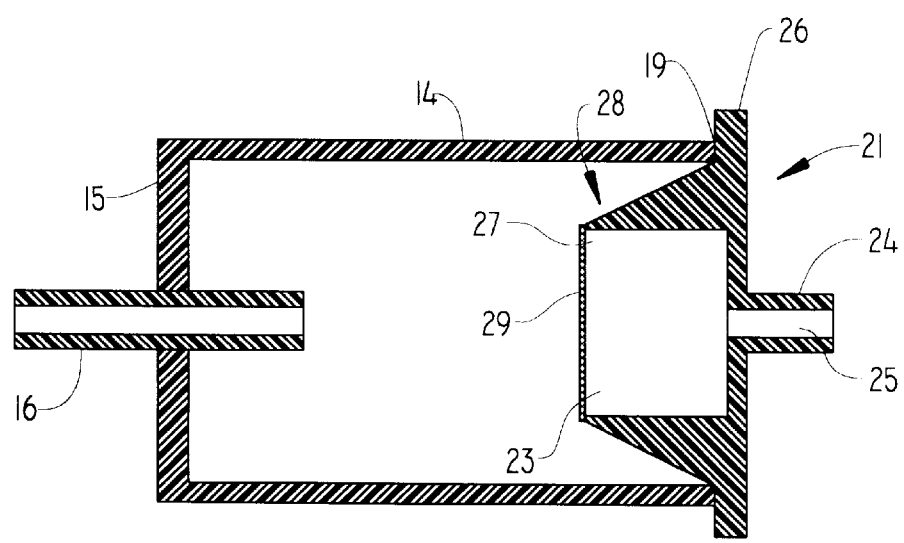
FIG. 2 is a cross section of the trap showing the filter therein.

The dental wand 10, shown in FIG. 1, is a hand held surgical instrument used by dentists and dental hygienists for removing air, saliva, wash liquid and debris from a patient's mouth during procedures such as cleaning the teeth. A connector 11 connects the wand 10 with a suction hose 12. The suction hose 12 is connected to a source of low pressure conventionally installed in dental offices. The suction may be controlled by a finger operated valve handle 13. The valve may be a flap valve for opening and closing the suction pathway in the connector 11.

The wand 10 has a transparent body 14 substantially cylindrical in shape. The forward end 15 of the body has a tubular suction tip connector 16 of smaller diameter than the wand body 14. The connector 16 extends into the interior of the wand body. The tip connector 16 is formed with a slight taper to accommodate a disposable suction tip 17.

The differential between the diameters of the body 14 and the connector 16 creates a discontinuity in the fluid flow. The heavier particulate material will separate from the air and liquid upon entering the body 14. The fluid mixture will exit through the exhaust tube 18.

The rear end 19 of the wand body 14 is formed with a circular opening 20 of substantially the same diameter as the cylindrical body. A tubular stopper 21 selectively closes the rear opening 20. The stopper 21 has an enlarged bore 23 within the wand body 14. The stopper terminates in a nipple 24 which has a smaller bore 25. The nipple 24 frictionally fits into the connector 11. The stopper has an annular flange 26 of greater diameter than the circular opening 20. The flange 26 acts as a stop during assembly of the wand and is used as a handle to disassemble the wand. The outer diameter of the stopper 21 that is disposed within the wand body is tapered inwardly from the flange 26 to the inner bore opening 27. This shape permits a conical cavity 28 ti surround the stopper 21 and form a receptacle for the particular material.

An absorbent filter material 29 may be placed in the wand body 14 to aid in the collection and display of the particulate material separated from the waste fluid. As shown, the absorbent material 29 may cover the inner bore opening 27 and extend into the conical cavity 28. The absorbent material may be woven or nonwoven cotton swatches. Other absorbent materials could be used, such as natural or synthetic foam pads.

In operation, the dental wand is used to evacuate the patient's mouth during the cleaning process. The wand entrains a mixture of air and liquids which include the tartar removed from the teeth by the cleaning implements. As the fluid enters the wand body, the tartar, in particulate form, separates from the fluids and falls to the bottom and sides of the wand body. The absorbent material supports the tartar and provides an easily removable substrate. for displaying the tartar.

When the operation is finished or when there is enough tartar to make a demonstration, the suction is shut off. The wand body is then opened by grasping the flange and the body. The absorbent material is then removed from the wand body with the entrapped particulate material to make an exhibit. The dentist or dental hygienist may then use the exhibit to explain the necessity for proper personal dental hygiene and demonstrate the results of poor practices.

It is to be understood that while a certain form of the invention is illustrated, it is not to be limited to the specific form or arrangement of parts herein described and shown. It will be apparent to those skilled in the art that various changes may be made without departing from the scope of the invention and the invention is not to be considered limited to what is shown and described in the specification and drawings.

What is claimed is:

1. A dental suction wand for collecting and displaying particulate material removed from a patient's teeth comprising a large diameter tubular wand body having a front end and a rear end, said body having a large diameter interior bore, a small diameter tubular tip connector extending from said front end of said body, a tip continuing into an interior of said body, said rear end of said body formed with a large diameter opening, a truncated conical shaped stopper with a bore therethrough frictionally engaging said opening, said stopper having a connection for a suction hose, said truncated stopper and said body forming a conical shaped cavity in said body for receiving the particulate material.

2. A dental suction wand of claim 1 wherein said stopper has a large diameter opening located in said interior of said body.

3. A dental suction wand of claim 2 wherein said body is transparent.

4. A dental suction wand of claim 3 wherein an absorbent filter covers said large diameter opening of said stopper.

5. A dental suction wand of claim 4 wherein said absorbent filter extends into said cavity.

6. A dental suction wand of claim 5 wherein said absorbent filter is removable.

7. A dental suction wand for collecting and displaying particulate material removed from a patient's teeth comprising a tubular connector for a dental suction hose, said connector having a manual valve for controlling the suction, said connector friction fit with a nipple formed on a truncated conical shaped stopper, said stopper having a bore extending therethrough, said stopper closing one end of an elongated large diameter wand body, an other end of said body having a small diameter tip connector extending therefrom, said tip connector adapted to operatively engage a dental suction tip.

8. A dental suction wand of claim 7 wherein said truncated conical shaped stopper and said body form a conical cavity and said truncated conical shaped stopper has a large diameter opening.

9. A dental suction wand of claim 8 wherein a removable absorbent filter covers said large diameter opening of said stopper and extends into said cavity.

10. A dental suction wand of claim 9 wherein said stopper has an annular flange engaging said one end of said wand body.

11. A method of demonstrating the effects of poor personal dental hygiene comprising the steps of
    (a) providing a dental suction wand having a large diameter body with a small diameter tip connector at one end and a truncated conical stopper with a bore therethrouqh closing the other end, said body and said truncated conical shaped stopper forming a cavity in said body, a removable absorbent filter in said cavity,
    (b) removing tartar from the teeth of a patient,
    (c) applying a wash liquid to the teeth,
    (d) inserting said suction wand into the wash liquid and entraining said wash liquid through said suction wand,
    (e) capturing said tartar on said filter,
    (f) removing said filter from said wand and
    (g) demonstrating the effects of poor dental hygiene to the patient by visual examination of said filter.

* * * * *